(12) United States Patent
Haddock et al.

(10) Patent No.: US 7,679,742 B2
(45) Date of Patent: Mar. 16, 2010

(54) METHOD, SYSTEM AND APPARATUS FOR MONITORING VARIATIONS IN THE SIZE OF PARTICLES PRESENT IN A FLUID

(75) Inventors: Thomas F. Haddock, Ann Arbor, MI (US); Mark Allen Dugan, Ann Arbor, MI (US); Ali Said, Ann Arbor, MI (US); Philippe Bado, Ann Arbor, MI (US)

(73) Assignee: Translume, Inc., Ann Arbor, MI (US)

( * ) Notice: Subject to any disclaimer, the term of this patent is extended or adjusted under 35 U.S.C. 154(b) by 351 days.

(21) Appl. No.: 11/712,274

(22) Filed: Feb. 28, 2007

(65) Prior Publication Data
US 2008/0204749 A1 Aug. 28, 2008

(51) Int. Cl.
*G01N 15/02* (2006.01)
(52) U.S. Cl. .................. 356/335; 356/336; 356/337; 356/341
(58) Field of Classification Search ......... 356/335–343, 356/70, 38, 432–442, 320, 326; 250/564, 250/573, 577; 73/53.05–54.01; 324/698
See application file for complete search history.

(56) References Cited

U.S. PATENT DOCUMENTS

| | | | | |
|---|---|---|---|---|
| 4,497,577 A | * | 2/1985 | Sato et al. ............... | 356/336 |
| 4,659,218 A | * | 4/1987 | de Lasa et al. ........... | 356/133 |
| 4,830,494 A | * | 5/1989 | Ishikawa et al. ......... | 356/336 |
| 5,185,641 A | * | 2/1993 | Igushi et al. ............. | 356/336 |
| 5,194,910 A | | 3/1993 | Kirkpatrick, Jr. et al. | |
| 2002/0135750 A1 | * | 9/2002 | Arndt et al. .............. | 356/28.5 |
| 2007/0242269 A1 | * | 10/2007 | Trainer ..................... | 356/336 |

OTHER PUBLICATIONS

U.S. Appl. No. 11/037,625, Said et al.

\* cited by examiner

*Primary Examiner*—Gregory J Toatley, Jr.
*Assistant Examiner*—Tri T Ton

(57) ABSTRACT

The present invention relates to a method, system and apparatus for continuously monitoring variations in the size of particles present in a fluid on a real time basis. The method comprises of passing one or more optical signal through the fluid such as engine oil. The variation (attenuation or enhancement) in the intensity of the optical signal is continuously measured with respect to time. In an embodiment, the method, system and apparatus of the present invention enable monitoring of the amount, size and onset of particle agglomeration using single or multiple wavelengths as interrogating optical signal(s). An exemplary embodiment is provided for monitoring of the amount, size and onset of soot particle agglomeration in engine oil using single or multiple wavelengths as interrogating optical signal(s).

30 Claims, 6 Drawing Sheets

METHOD, SYSTEM AND APPARATUS FOR MONITORING VARIATIONS IN THE SIZE OF PARTICLES PRESENT IN A FLUID

STATEMENT OF GOVERNMENT SUPPORT

The present invention was made with government support under contract No. W56HZV-04-C-0009 awarded by the US Army. The government has certain rights in the invention.

The present invention is related to a prior patent application "Optical Sensing of Fluid Condition—Method and Apparatus" U.S. Ser. No. 11/037,625 filed Jan. 18, 2005

FIELD OF INVENTION

The present invention relates generally to the monitoring of variations in size of particles present in a fluid. More particularly, the present invention relates to methods and systems for monitoring variations in the size of particles present in a fluid by optical means.

BACKGROUND OF THE INVENTION AND PRIOR ART

Monitoring the size and amount of particles or contaminants present in a fluid is important in various industrial applications. This can be achieved by utilizing direct or indirect optical measurement methods, including scattering methods.

Scattering is a general physical phenomenon whereby some forms of radiation, such as light or moving particles, are forced to deviate from a straight path by one or more localized non-uniformities in the medium through which it passes. The types of non-uniformities that can cause scattering are sometimes known as scatterers or scattering centers. The scatterers may include particles, bubbles, droplets, density fluctuations in fluids, defects in crystalline solids, surface roughness, cells in organisms, and textile fibers in clothing etc. Scattering is a very general phenomenon which can take various forms depending on the size of the scatterer as compared to the wavelength of the radiation.

As known in art the scattering phenomenon can be categorized as Rayleigh scattering or Mie scattering. Rayleigh scattering involves scattering of light, or other electromagnetic radiation, by particles significantly smaller than the wavelength of the light. For particle sizes comparable to or somewhat larger than the interrogating wavelength, Mie scattering predominates. At values of the ratio of particle diameter to wavelength more than about 10, the laws of geometric optics are mostly sufficient to describe the interaction of light with the particle, and at this point the interaction is not usually described as scattering.

Known optical methods for different applications use various wavelengths including wavelengths that are smaller, about the same as or larger than the size of the particles to be measured. One such application is to monitor the amount and size of soot particles in engine lubricating oil (hereafter referred to as 'engine oil') wherein the intensity of the interrogating optical signal when passed through the engine oil containing non-uniformities/particulate material can be analyzed to monitor the condition of the engine oil.

In standard internal combustion engines, most of the soot generated by the combustion of the fuel is released to the atmosphere via the exhaust gas, while a small fraction entered the crankcase and the engine lubricant via combustion gas blow-by (i.e. combustion gas leaking pass the piston rings, valve guides, etc.), or through deposition on cylinder walls that was subsequently scraped off by the piston rings and ultimately deposited into the lubricating oil. Further, due to more rigorous nitro-oxidation and hydrocarbon emission policies of the environmental protection agencies, engine manufacturers are increasingly using exhaust gas recirculation (EGR) to reduce atmospheric soot emissions. EGR sends some of the engine emissions, including soot, back to the combustion chamber creating a multi-pass opportunity for the soot to ingress to the lubricating oil and thereby increasing the rate of growth of soot concentration in the lubricant.

For most combustion engines, the soot content (or soot load or soot weight) increases more or less linearly with the number of hours of operation since the last oil change. As time progress the amount of soot trapped in the engine oil can reach significant levels, especially in Diesel engines. Under some conditions the accumulation of soot in the engine oil can prevent proper lubrication of the engine parts and can significantly accelerate engine wear. It is therefore important to be able to monitor the presence of soot and/or other contaminations in internal combustion engines and/or any other device where such particles may be present. Soot particles comprise the largest volume of contaminants present in used diesel engine lubrication oil. When large amount of soot is present, the lubricating oil viscosity is altered, and the oil may no longer be able to properly lubricate the engine. Furthermore large agglomerated soot particles cause abrasive action on the engine bearings. This is most insidious in regions of high-load where oil films are on the order of microns or less.

In fresh lubricating oil, the soot particles are suspended in the oil, surrounded by additives such as dispersants whose function is to prevent soot particle growth. When the dispersant is consumed or prevented to perform its function, the small soot particles can aggregate to form much larger elements. The risk to the engine is limited as long as these small soot particles remain suspended in the oil and are not allowed to agglomerate to form larger particles. However, when the soot particles grow to be of a size similar to that of the lubricating oil film thickness as found on critical parts, significant wear to the engine may rapidly occur. This condition is highly undesirable and there has been a need for systems to monitor the condition of the engine oil so that damages associated with the wear due to contaminated engine oil can be avoided or minimized.

Some of the prior art systems monitor condition of the engine oil by indirect measurements, for example by measuring surrogates, such as dielectric constant. However, these surrogates may be influenced by many parameters besides soot such as moisture, ethylene glycol, etc. It is difficult to assess the state of the engine oil using these indirect measurements.

The U.S. Pat. No. 5,309,213 titled, "Optical determination of amount of soot in oil sample" assigned to Desjardins, John B. et al., proposes a method and apparatus for determining the concentration of materials in fluids, such as soot in diesel engine lubricating oils. An optical cell is employed in the form of a very thin tapered sample volume which is inserted into a light beam. The attenuation of the beam is measured at different locations along the varying thickness of the sample. The invention of Desjardins, et al is focused towards an improved optical cell for determining soot concentration in engine oil. Desjardin's monitor the optical transmission at one point in time. This approach does not provide information about the soot particles physical size, or the soot particle growth. Furthermore Desjardin's approach requires movement of the analytical cell in order to perform the measurement.

There is therefore a need for a method and system for a real-time and in-field monitoring the condition of soot particles present in the engine oil in order to minimize potentially high-risk circumstances of wear and damage of the engine.

SUMMARY

Accordingly an aspect of the present invention provides a method and a system for optically monitoring an increase in the size of particles present in a fluid. The onset of a particle size build-up process can be detected by monitoring the intensity of the interrogating optical signal(s) with respect to time, on a frequent-basis or constant-basis.

In order to meet the above criteria, the method comprises passing at least one optical signal of distinct predetermined wavelength, through the fluid, and detecting the power of the signal exiting the fluid. The method thereafter measures an attenuation in an intensity corresponding to each optical signal with respect to time along or near the axis of the main optical path. In response to measuring the attenuation, the method determines the size of particles is more than a threshold size of particles if the rate of change of the attenuation in the intensity of the optical signal is more than a threshold rate of change of attenuation in the intensity. The step of determining the size of particles comprises determining a first slope and a second slope of an attenuation in intensity-time graph at a first predetermined time and a second predetermined time respectively. The step of determining further comprises detecting an occurrence when the second slope becomes substantially larger from the first slope and flagging an instance corresponding to the occurrence in response to detecting. In an embodiment the optical signal does not pass directly through the fluid but rather samples it through its evanescent field.

Another object of the present invention is to provide a method, system and apparatus for monitoring a decrease in size of particles present in a fluid. The method comprises passing at least one optical signal of a distinct predetermined wavelength through the fluid, and detecting the power of the signal exiting the fluid. Thereafter, the method measures an enhancement in an intensity corresponding to each optical signal at a corresponding predetermined wavelength with respect to time along or near the axis of the main optical path. In response to measuring, the method determines the size of particles is less than a threshold size of particles in response to measuring if the rate of change of the enhancement in the intensity of the optical signal is less than a threshold rate of change of the enhancement in the intensity. The step of determining the size of particles comprises determining a first slope and a second slope of an intensity-time graph at a first predetermined time and a second predetermined time respectively. The step of determining further comprises detecting an occurrence when the second slope becomes substantially less than the first slope and flagging an instance corresponding to the occurrence in response to detecting.

It is another object of the present invention to provide a method, system and apparatus for monitoring variations (increase or decrease) in the size of particles present in the fluid wherein the attenuation or enhancement in the intensity is monitored with reference to time, on a real time basis.

It is another object of the present invention to provide a method, system and apparatus for monitoring variations (increase or decrease) in the size of soot particles present in an engine oil. The soot particles comprising carbon particles and/or aggregates of carbon particles.

It is yet another object of the present invention to provide a system for monitoring variations (increase or decrease) in the size of particles present in a fluid. The system comprises an optical signal passing means and a measuring means. The optical signal passing means passes at least one optical signal of a distinct predetermined wavelength through the fluid, and detecting the power of the signal exiting the fluid. The measuring means measures the variations (attenuation or enhancement) in intensity with respect to time along the axis of the main optical path. The system further comprises a determining means configured to determine a first slope and a second slope of an intensity-time graph at a first predetermined time and a second predetermined time respectively. Thereafter, the determining means detects an occurrence when the second slope becomes substantially different from the first slope and flags an instance corresponding to the occurrence in response to detecting.

In an embodiment, the determining means is further configured to determine if the size of particles is more than a threshold size of particles; and determine if a rate of change of the attenuation in the intensity of the optical signal is more than a threshold rate of change attenuation in the intensity. The measurements are taken at a predetermined sampling frequency. In another embodiment, the determining means is configured to determine if the size of particles is less than a threshold size of particles; and determine if a rate of change of the enhancement in the intensity of the optical signal is less than a threshold rate of change of enhancement in the intensity. The measurements are taken at a predetermined sampling frequency.

It is another object of the present invention to provide a method for optically monitoring an increase or decrease in the size of soot particles present in the engine oil. The onset of a soot agglomeration process can be detected by monitoring the intensity of the interrogating optical signal(s) with respect to time, on a frequent-basis or constant-basis.

In accordance with an overall aspect of the present invention it is recognized that a single measurement is insufficient to provide sufficient data to irrevocably identify the onset of the particle size build-up or soot agglomeration. Accordingly an aspect of the present invention provides a system that provides a time-sequence of the intensity of the interrogating beam to conclusively identify the onset of the agglomeration. This time-sequence data offers information not obtainable with traditional laboratory equipment and standard laboratory methods where data is collected at one fixed time. The optical signal is monitored continuously or quasi-continuously. The attenuation in the intensity as function of time is processed with an algorithm that detects a substantial change (increase in attenuation) in slope of the attenuation in intensity-time graph. The substantial change in slope corresponds to the agglomeration of soot particles.

It is another object of the present invention to provide a method wherein two or more optical signals of the distinct predetermined wavelengths are passed through the fluid, and detecting the power of the signals exiting the fluid. The use of two or more wavelengths is advantageous as combined data is less susceptible to noise associated with data acquisition and with noise created by other types of contaminants (metal particles, air bubbles, etc.). Further, the combined data can provide a first warning signal (for example, first detection of aggregation onset) indicating that the onset process is starting followed by a second signal (second detection of aggregation onset). The time interval between these two signals indicates the rate of aggregation of particles present in the fluid.

BRIEF DESCRIPTION OF THE FIGURES

The accompanying figures where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
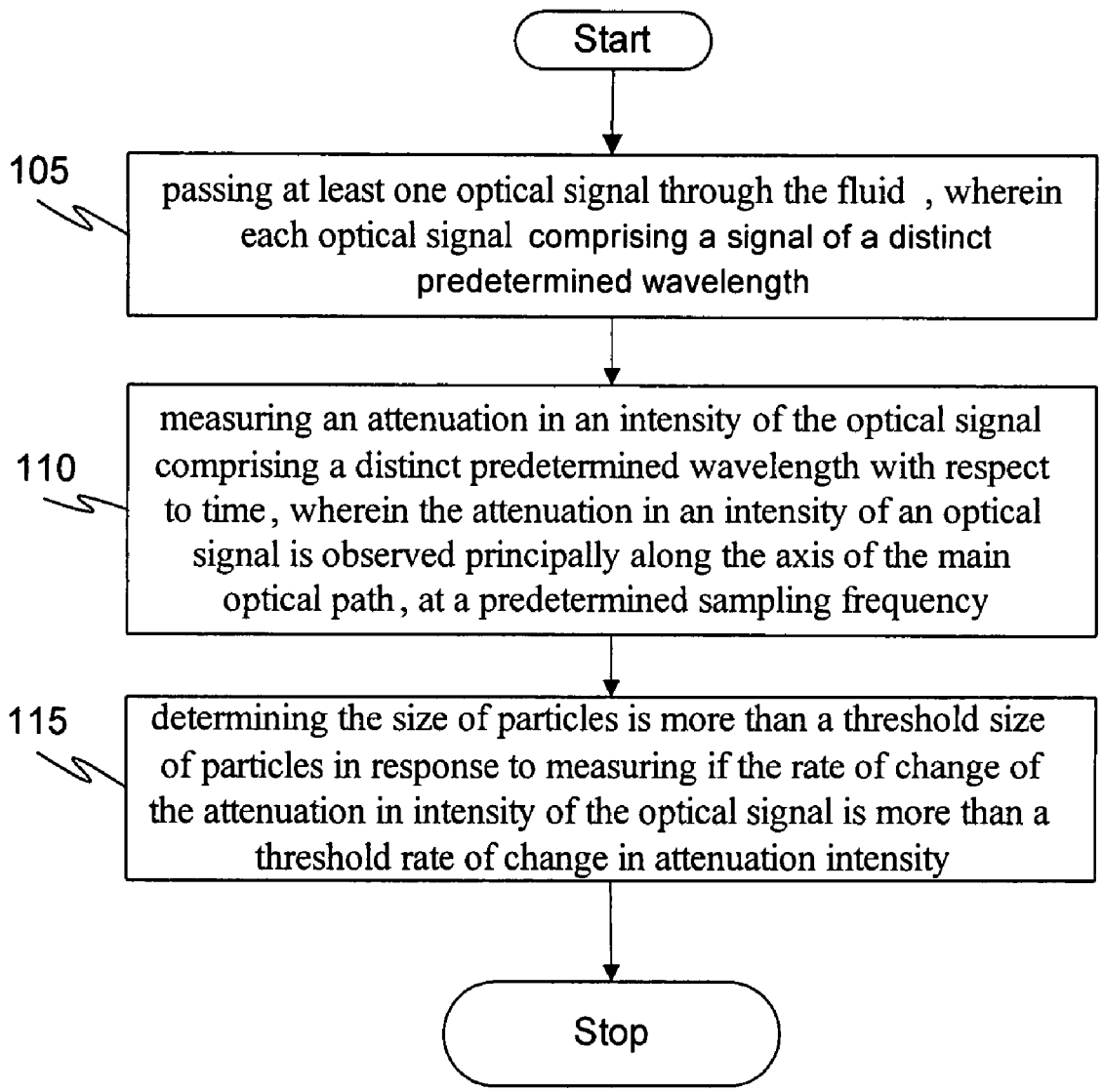
FIG. 1 illustrates a flow diagram of a method for monitoring an increase in the size of particles present in a fluid in accordance with an embodiment of the present invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION OF THE INVENTION

Before describing in detail embodiments that are in accordance with the present invention, it should be observed that the embodiments reside primarily in combinations of method steps and system components related to a method, system and apparatus for monitoring variations in the size of particles present in a fluid. Accordingly, the system components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

The present invention may be embodied in several forms and manners. The description provided below and the drawings show exemplary embodiments of the invention. Those of skill in the art will appreciate that the invention may be embodied in other forms and manners not shown below. The invention shall have the full scope of the claims and is not to be limited by the embodiments shown and described below.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Various embodiments of the present invention provide a method, system and apparatus for monitoring variations in the size of particles present in a fluid by direct optical measurements. In an embodiment, the method, system and apparatus of the present invention enable monitoring of onset of particle size build-up process. The variation (attenuation or enhancement) in the intensity of the interrogating optical signal of a predetermined wavelength is measured with respect to time. In an embodiment, the attenuation in the intensity of the optical signal is measured with respect to time and then the onset of particle size build-up is detected, based on a substantial change in the rate of change of the attenuation in the intensity. By monitoring both density and agglomeration over time, the information provided by the system and method of the present invention allows for intervention at the optimal time before significant damage can occur.

An embodiment of the invention enables monitoring of the amount and size of soot particles present in the engine oil and continuous monitoring of onset of soot agglomeration on a real time basis. Real-time, on-line soot state monitoring system of the present invention is based on direct optical measurements. This is in contrast to other systems that measure surrogates, such as dielectric constant, which may be influenced by many parameters besides soot. Real-time data gives time-sequence data of the intensity of the interrogating optical signal that is significantly more valuable than single-value data. The value of this data exceeds simple averaging of single-value data, and offers information not obtainable with traditional laboratory equipment. Various phenomena such as absorption, side-scattering, back-scattering, etc. attenuate the interrogating optical signal. The amount of attenuation is a function of the amount of soot particles present in the sample and also on the size of the soot particles.

FIG. 1 is a flow diagram illustrating a method for monitoring an increase in the size of particles present in a fluid of interest in accordance with an embodiment of the present invention. The method comprising passing one or more optical signals through the fluid at step 105. In an embodiment of the present invention, each optical signal comprises a signal of a distinct predetermined wavelength. A distinct predetermined wavelength of an optical signal can be selected from a range of about 400 nm to 1700 nm. In another embodiment of the present invention, a distinct predetermined wavelength of an optical signal can be selected from any one or any combination of about 840 nm, 980 nm and 1550 nm.

It would be apparent to a person skilled in the art that while a single wavelength can provide the desired information about the particle density and onset of particle size build-up process, it is advantageous to pass two or more wavelengths through the fluid. Combined data obtained in a method utilizing two or more wavelengths through the fluid are less susceptible to noise associated with data acquisition and noise created by other types of contaminants. Further, the method can provide a first warning signal (first detection of aggregation onset) to indicate that the onset process is starting followed by a second signal (second detection of aggregation onset). The time interval between these two signals indicates the rate of agglomeration which by itself can be a very useful piece of information. The onset of agglomeration appears later for the longer wavelengths. Also, the method utilizing two or more wavelengths can be also useful to measure absolutely the build-up of soot content prior to soot agglomeration. In an embodiment of the present invention, a wavelength corresponding to an optical signal is selected on the basis of at least one of the size of the particles present in the fluid, optical characteristics of the particles present in the fluid and the refractive index of the fluid.

The fluid, through which the interrogating optical signal is passed, may contain elements susceptible to aggregate or that form colloids. In an exemplary embodiment of the present invention, the soot particles are of primary interest. For example in the food industry mayonnaise may fall in this group. In case of the pharmaceutical industry various ointment, sun block, antacid, etc. are examples where constituents may aggregate. In the printing industry inks are example where one may want to monitor aggregation. Therefore, the present invention encompasses all such variants of the method to continuously monitor size, amount and state of particles where aggregation is a factor. It would be apparent to a person skilled in art that, the fluid of interest may be any fluid that contains particles susceptible to aggregate or change size, including engine oil, hydraulic oil, electrical insulating oil, etc.

Reference back to the FIG. 1, at step 110, attenuation in intensity of an optical signal comprising a signal of a distinct predetermined wavelength is measured with respect to time. In an embodiment, a source of optical signal with a broad range of wavelengths is used and a wavelength selection means (e.g. a narrow bandpass filter) is placed ahead of a detector. In another embodiment, a source of optical signal with a narrow range of the desired wavelength is used with a broad wavelength detector. In either case the combined optical source and detector assembly is configured so that only the wavelength of interest is monitored. The attenuation in the intensity of an optical signal is observed principally along an axis of the main optical path at a predetermined sampling frequency. In an embodiment of the present invention the predetermined wavelength is selected so as to keep the ratio of the size of the particles to the wavelength, in a predetermined range. In an exemplary embodiment of the present invention, the predetermine wavelength is selected so as to keep the ratio of the size of the particles to the wavelength, in a range of about 0.3 to 8.0. In an embodiment, the measurements are done on a long-time basis to observe and monitor the overall trend. The trend is expressed as the slope of the attenuation in intensity-time graph that is monitored to reflect substantial variations in particle size.

It would be apparent to a person skilled in the art that variation in the intensity between the sample of small particles and large particles is a function of an observation angle. For example, when observing the optical signal from the back or from the side, the respective effects of the small and large particles on the optical signal being observed may drastically change. In an embodiment of the present invention, variation (attenuation or enhancement) is measured principally in a forward-looking configuration. Further, the attenuation in the intensity can be measured with reference to a number of hours of operation of an engine utilizing the engine oil or with reference to a number of revolutions of the engine utilizing the engine oil. In another embodiment of the present invention, the attenuation in the intensity can be measured with reference to a number of miles traveled by a vehicle with the engine utilizing the engine oil. In yet another embodiment of the present invention, the attenuation in the intensity is measured with reference to the age of the engine oil.

At step 115, it is determined if the size of particles is more than a threshold size of particles if the rate of change of attenuation in the intensity of the optical signal is more than a threshold rate of change of attenuation in the intensity. A significant rate of change of the attenuation in the intensity indicates the process of agglomeration for example in case of soot particles present in engine oil. At this point, the density of the soot-particles becomes high enough to overcome effectiveness of a dispersant present in the engine oil and beyond this point the dispersant may not be able to prevent the growth/agglomeration of the soot particles present in the fluid. Alternatively the dispersant may have become depleted. The determining step 115 is further explained in detail in conjunction with FIG. 2

Figure 2:
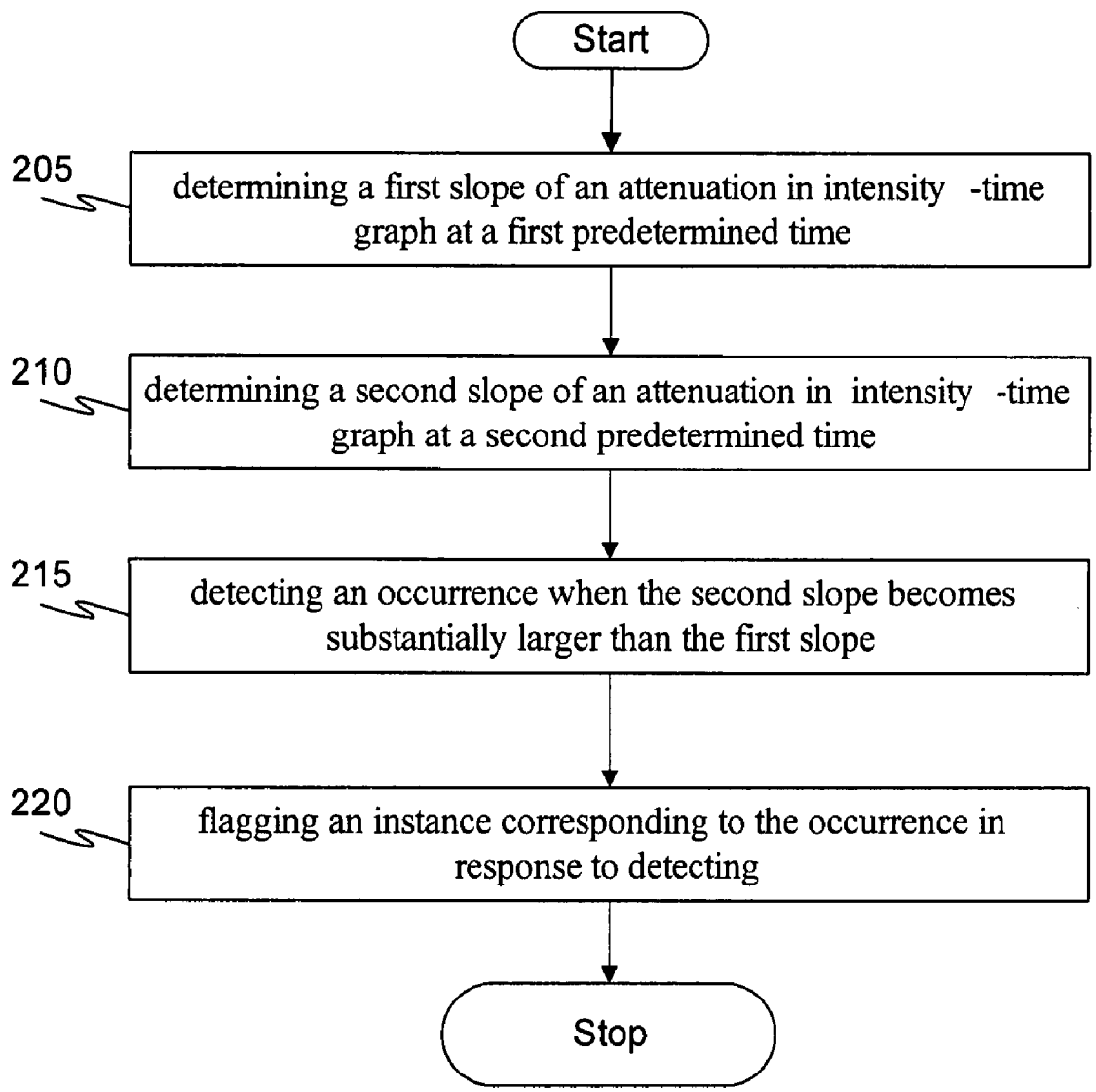
FIG. 2 illustrates flow diagram of the step of determining the size of particles with respect to a threshold size in response to measuring the attenuation in the intensity with an embodiment of the present invention.

FIG. 2 is a flow diagram illustrating the method of determining the size of particles with respect to a threshold size in response to measuring the attenuation in the intensity in accordance with an embodiment of the present invention. At step 205 a first slope of an attenuation in intensity-time graph is determined at a first predetermined time. Further, at step 210 a second slope of the attenuation in intensity-time graph is determined at a second predetermined time. At step 215 an occurrence is detected when the second slope becomes substantially larger than the first slope. In an embodiment the slope of the intensity-time graph is monitored for the soot particles present in the diesel engine oil reflecting a very significant change. In case of weaker slope change, the noise levels have to be reduced by averaging-out the data to eliminate short-term fluctuations in order to monitor small changes in slope of the intensity-time graph.

In an embodiment of the present invention, the flow of the data, for example the attenuation in intensity as a function of time is processed with an algorithm that looks out for a substantial change in slope of the intensity-time graph. For example, when the attenuation in the intensity is measured with reference to time, a substantial increase in the slope corresponds to the agglomeration of the particles. In another embodiment of the present invention, the algorithm enables averaging out the data to eliminate short-term fluctuations due to presence of air-bubbles or other impurities. In yet another embodiment, the algorithm enables adjusting the data for changes associated with drift of the optical source used. This requires monitoring of the optical source used prior to its entry into the sample.

Thereafter, an instance corresponding to the occurrence is flagged at step 220 in response to detecting. In an embodiment, the method provides a time-sequence data of the attenuation in intensity of the interrogating optical signal to conclusively identify the onset of agglomeration. The optical signal is monitored continuously or quasi-continuously. In an embodiment the measurements are taken on a continuous basis however the frequency of the data sampling may be lower in order to avoid overfilling the memory space. In an embodiment the data is saved every few minutes to every hour. The data is averaged over some period of time and the averaging period depends upon the type of the application, and the system noise level.

Prior to the agglomeration onset, the data can be analyzed and the absolute amount of the particles present can be extracted. This can be done by the application of the Beer-Lambert Law (Beer's law) since before agglomeration all soot particles are of approximately similar size. Hence the particulate scattering efficiency is constant throughout the pre-agglomeration regime. After the onset of the soot agglomeration it is much more difficult to extract the absolute soot weight content as the relation between detected signal strength and the number and size of the particles changes. As the size of the particles changes, so does the corresponding scattering cross-section (i.e. scattering efficiency). As a result it becomes difficult to deconvolve the soot concentration by weight from the scattering data.

Figure 3:
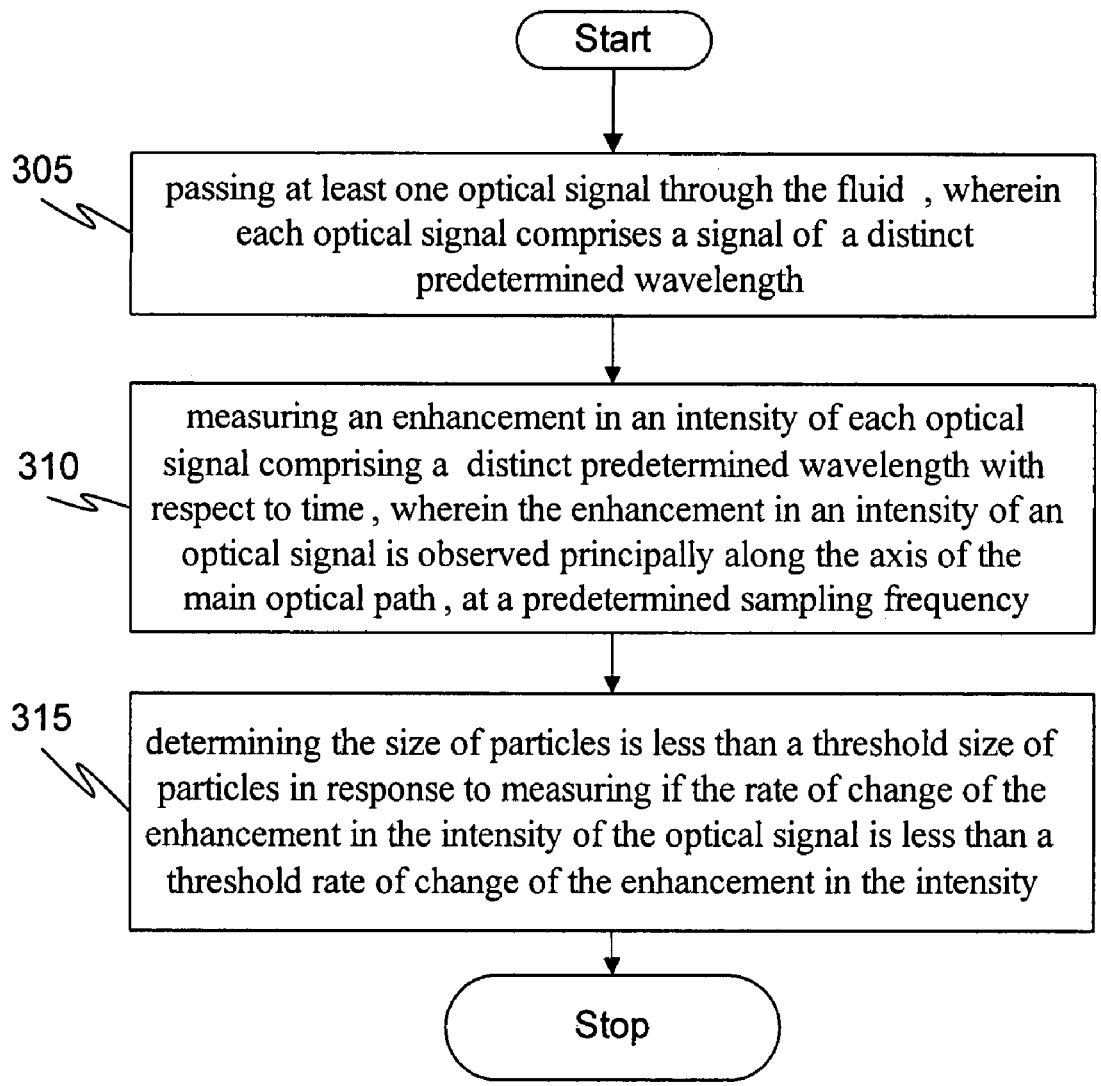
FIG. 3 illustrates a flow diagram of a method for monitoring a decrease in the size of particles present in a fluid with an embodiment of the present invention.

FIG. 3 is a flow diagram illustrating a method for monitoring a decrease in the size of particles present in a fluid of interest in accordance with an embodiment of the present invention. The method comprising passing one or more optical signals through the fluid at step 305. In an embodiment of the present invention, each optical signal comprises a signal of a distinct predetermined wavelength. A distinct predetermined wavelength of an optical signal can be selected from a range of about 400 nm to 1700 nm. In another embodiment of the present invention, a distinct predetermined wavelength of an optical signal can be selected from any one or any combination of about 840 nm, 980 nm and 1550 nm. An example would be soot particles in dirty engine oil to which clean oil with plenty of fresh dissolving additive, is added. The new additives could reverse the aggregation phenomenon, dissolving the large particles into smaller particles. Another example is a solution containing large particles that are mechanically crushed into smaller particles.

It would be apparent to a person skilled in the art that while a single wavelength can provide the desired information about the particle density and onset of particle size reduction process, it is advantageous to pass two or more wavelengths through the fluid. Combined data obtained in a method utilizing two or more wavelengths through the fluid are less susceptible to noise associated with data acquisition and noise created by other types of contaminants. Further, the method can provide a first warning signal (first detection of dissolution onset) to indicate that the onset process is starting followed by a second signal (second detection of dissolution onset). The time interval between these two signals indicates the rate of dissolution which by itself can be a very useful piece of information. The onset of dissolution (or size reduction) appears later for the shorter wavelengths and the delay between the detection of the onset corresponding to two interrogating wavelengths may be quite short and will be a function of the respective ratio of wavelength to particle size (wavelength/particle size).

Reference back to the FIG. 3, at step 310, enhancement in intensity corresponding to each optical signal is measured at a corresponding predetermined wavelength with respect to time. The enhancement in the intensity of an optical signal is observed along an axis of the main optical path at a predetermined sampling frequency. In an embodiment of the present invention the predetermined wavelength is selected so as to keep the ratio of the size of the particles to the wavelength, in a predetermined range. In an exemplary embodiment of the present invention, the predetermine wavelength is selected so as to keep the ratio of the size of the particles to the wavelength, in a range of about 0.3 to 8.0.

It would be apparent to a person skilled in the art that variation in the intensity between the sample of small particles and large particles is a function of an observation angle. In an embodiment the variation (attenuation or enhancement) in intensity of an optical signal is observed principally along the axis of the main optical path.

At step 315, it is determined if the size of particles is less than a threshold size of particles if the rate of change of the enhancement in the intensity of the optical signal is less than a threshold rate of change of the enhancement in the intensity. A significant decrease in the rate of change of the enhancement in the intensity indicates the process of dissolution or size reduction. The determining step 315 is further explained in detail in conjunction with FIG. 4

Figure 4:
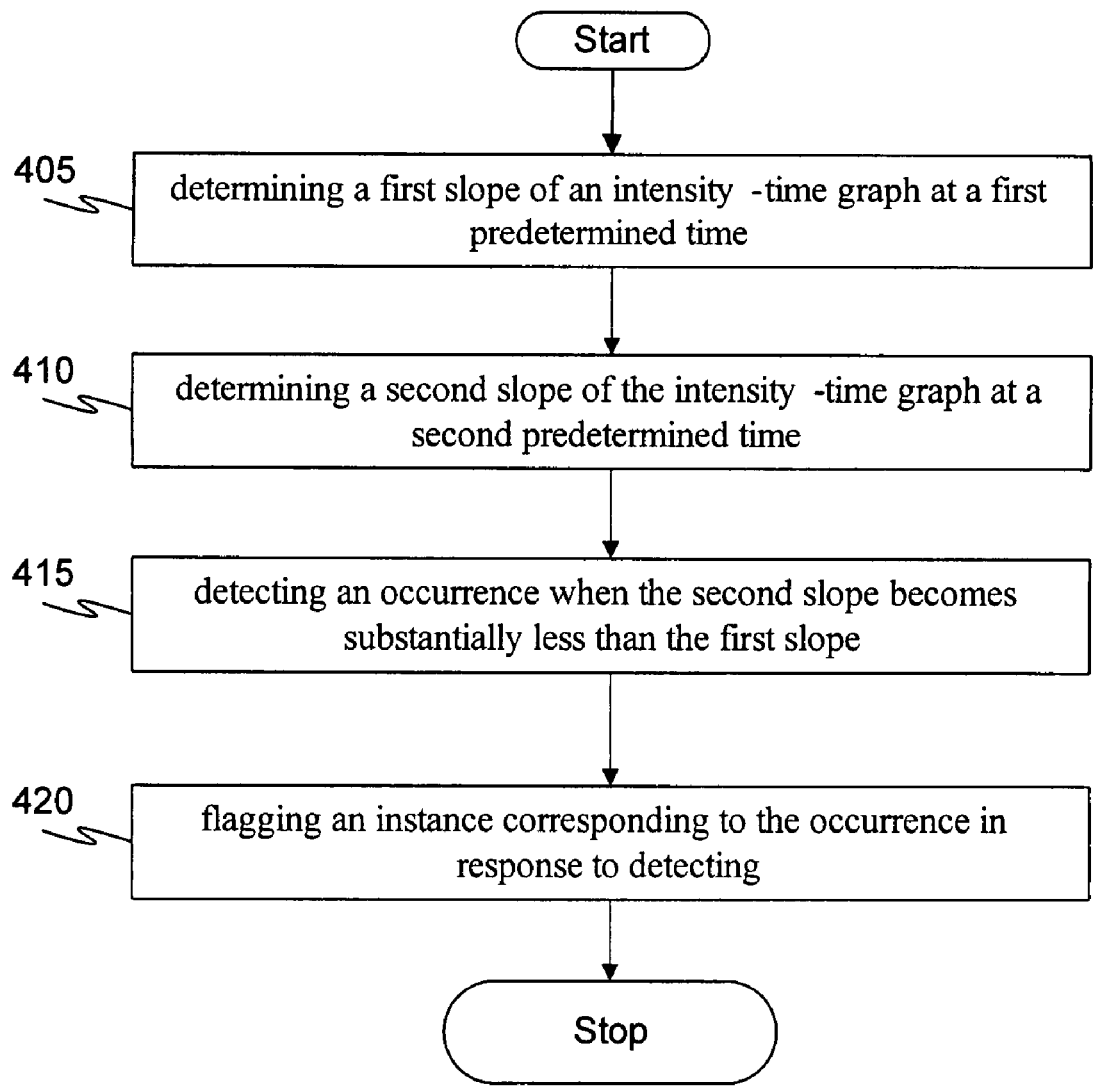
FIG. 4 illustrates flow diagram of the step of determining the size of particles in response to measuring the enhancement in the intensity with an embodiment of the present invention.

FIG. 4 is a flow diagram illustrating the method of determining the size of particles in response to measuring the enhancement in the intensity in accordance with an embodiment of the present invention. At step 405 a first slope of an intensity-time graph is determined at a first predetermined time. Further, at step 410 a second slope of the intensity-time graph is determined at a second predetermined time. At step 415 an occurrence is detected when the second slope becomes substantially less than the first slope.

Thereafter, an instance corresponding to the occurrence is flagged at step 420 in response to detecting. In an embodiment, the method provides a time-sequence data of the enhancement in the intensity of the interrogating optical signal to conclusively identify the onset of dissolution. The optical signal is monitored continuously or quasi-continuously.

Figure 5:
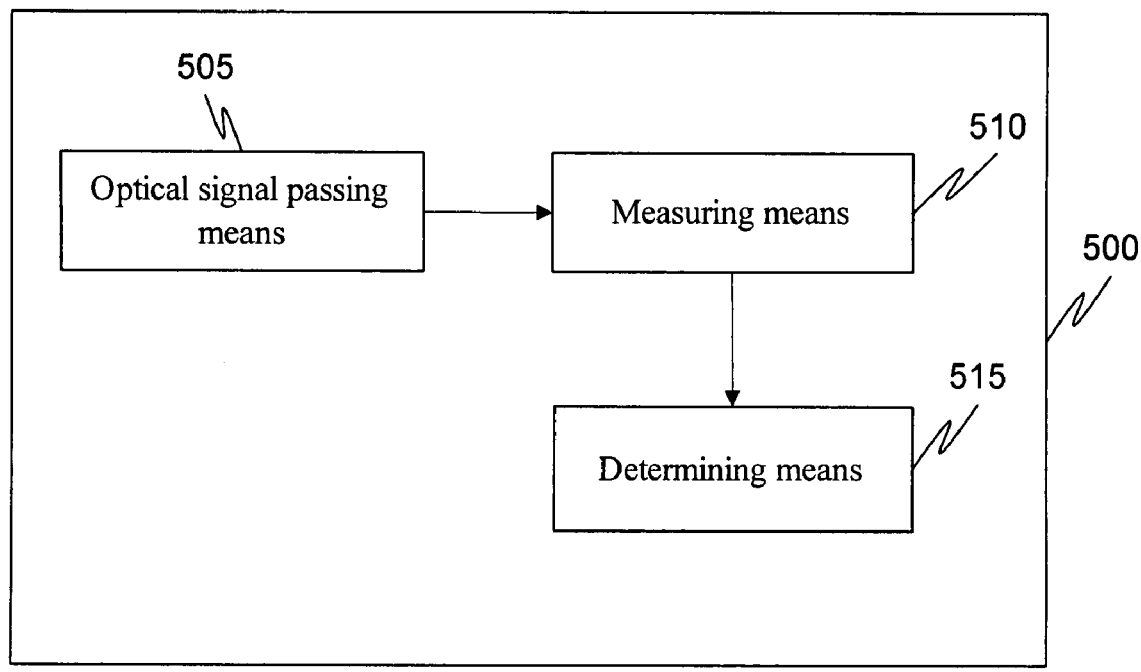
FIG. 5 is a block diagram showing a system for monitoring variations (increase or decrease) in size of particles present in a fluid with an embodiment of the present invention.

FIG. 5 is a block diagram showing a system 500 for monitoring variations (increase or decrease) in size of particles present in a fluid in accordance with an embodiment of the present invention. System 500 comprises an optical signal passing means 505, a measuring means 510 and determining means 515.

Optical signal passing means 505 passes one or more optical signals through the fluid. In an embodiment of the present invention each optical signal comprises a signal of a distinct predetermined wavelength. A distinct predetermined wavelength of an optical signal can be selected from a range of about 400 nm to 1700 nm. In another embodiment of the present invention, a distinct predetermined wavelength of an optical signal can be selected from any one or any combination of about 840 nm, 980 nm and 1550 nm.

Measuring means 510 measures variation in an intensity of an optical signal comprising a signal of a distinct predetermined wavelength with respect to time. In an embodiment, a source of optical signal with a broad range of wavelengths is used and a wavelength selection means (e.g. a narrow band-pass filter) is placed ahead of the detector. In another embodiment,—an optical source with a narrow range of the desired wavelength is used with a broadband wavelength detector. In either case, the combined optical source and detector assembly is configured so that only the wavelength of interest is monitored.

In an embodiment of the present invention the variation can be one of an attenuation and enhancement. The attenuation or enhancement in the intensity of an optical signal is observed principally along the axis of the main optical path, at a predetermined sampling frequency.

Determining means 515 is configured to determine a first slope of an intensity-time graph at a first predetermined time and a second slope of the intensity-time graph at a second predetermined time. Determining means 515 is further configured to detect an occurrence when the second slope becomes substantially different from the first slope. Upon detection of the occurrence, determining means 515 flags an instance corresponding to the occurrence in response to detecting. In an embodiment the attenuation in intensity as a function of time is processed with an algorithm that looks for a substantial change in slope of in the attenuation in intensity-time graph. An increase in the slope corresponds to the agglomeration. In another embodiment the enhancement in intensity as a function of time is processed with an algorithm that looks for a substantial change in slope of intensity-time graph. A decrease in the slope corresponds to the dissolution of the particles.

In an embodiment of the present invention, determining means 515 is further configured to determine if the size of particles is more than a threshold size of particles and thereafter determine if a rate of change of the attenuation in the intensity of the optical signal is more than a threshold rate of change of the attenuation in the intensity. In another embodiment of the present invention, determining means 515 is configured to determine if the size of particles is less than a threshold size of particles and thereafter determine if a rate of change of the enhancement in the intensity of the optical signal is less than a threshold rate of change of the enhancement in the intensity. The system can be adapted by fine-tuning the algorithms to suit specific application/wavelengths.

An embodiment of the present invention is based on a monolithic device described (in part) in a previous related application U.S. Ser. No. 11/037,625 filed Jan. 18, 2005. Various embodiments of the related application provide a system and method for determining a condition of a fluid. The method comprising collecting a fluid sample in-line from a fluid flow; and, measuring a plurality of optical properties of the fluid sample simultaneously. The optical properties are measured by sensing variations in the condition of the fluid continuously with respect to time.

In an embodiment of the present invention, system 500 may further comprise an averaging means for steadying the optical signal. The averaging means eliminates a fluctuation in the optical signal for steadying the optical signal.

In an embodiment, an algorithm enables averaging out the data to eliminate short-term fluctuations due to presence of air-bubbles or other impurities. In yet another embodiment, the algorithm enables adjusting the data for changes associated with drift of the optical source used. This requires monitoring of the optical source used prior to its entry into the sample.

Figure 6:
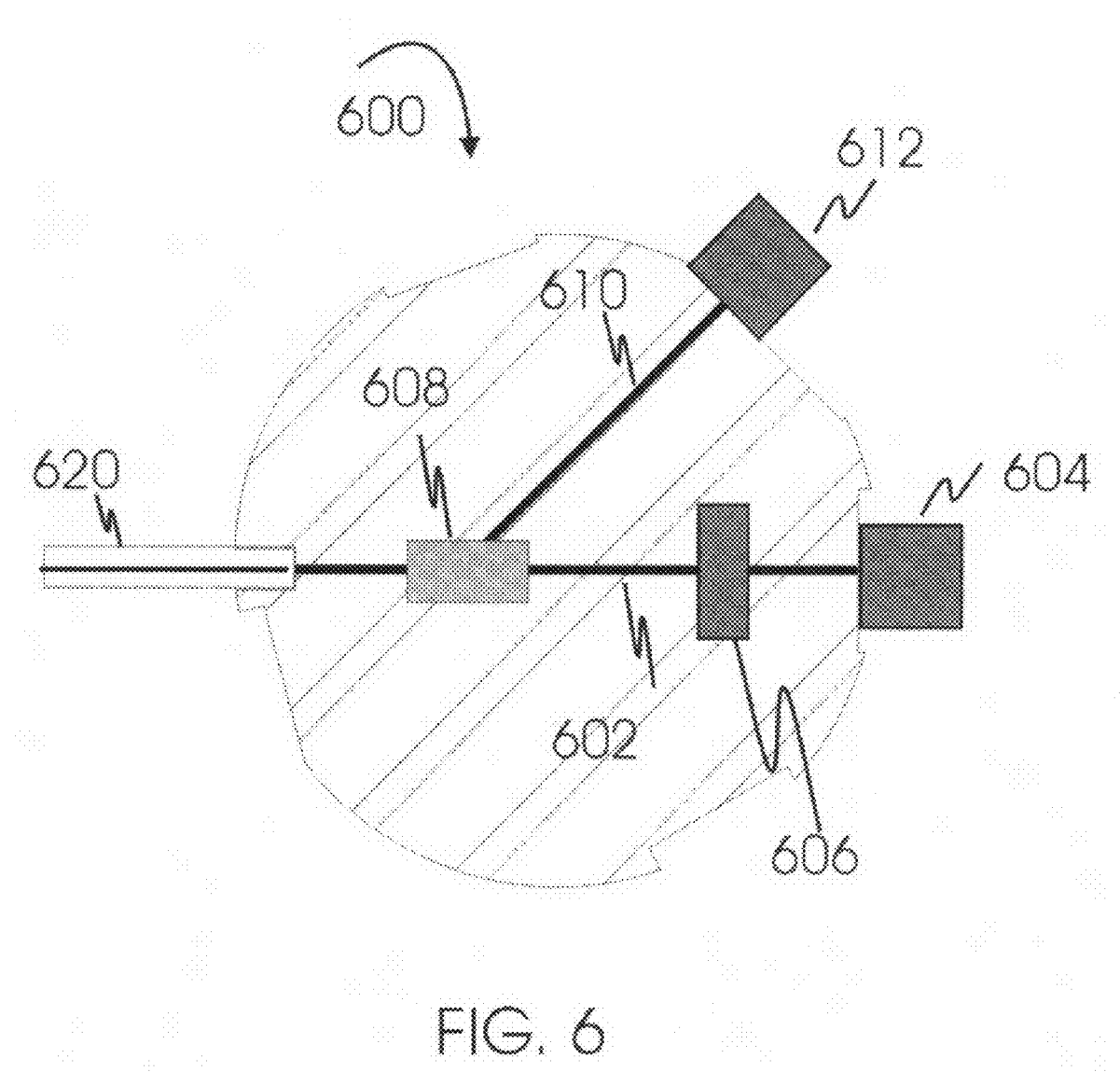
FIG. 6 is a diagram illustrating an apparatus for optically monitoring variations (increase or decrease) in size of the particles present in a fluid in accordance with an embodiment of the present invention.

FIG. 6 is a diagram illustrating an apparatus 600 for optically monitoring variations (increase or decrease) in size of the particles present in a fluid in accordance with an embodiment of the present invention. Apparatus 600 comprises an optical source (not shown in the figure) emitting at least one optical signal wherein each optical signal comprises a signal of a distinct predetermined wavelength. The light source signal propagates along path 602. Apparatus 600 further comprises a detector 604 and an analytical chamber 606. One or more detectors 604 detect optical signal(s) coming from path 602. Analytical chamber 606 is provided between the optical source, and detector 604 to contain the fluid of interest. In an embodiment of the present invention, apparatus 600 also comprises a splitter 608 to split the optical signal partially into a secondary optical path 610 provided prior to analytical chamber 606. One or more detectors 612 detect optical signal(s) coming from path 610. Splitter 608, optical path 610, and detector 612 provide a mean to monitor the output from the optical source, correct for unwanted changes in or failure of the optical source output. The optical source and the detector together are sensitive only to the distinct predetermined wavelength and the optical source and the detector being operable to measure the rate of change of the intensity of the optical signal at the distinct predetermined wavelength.

In another embodiment of the present invention, apparatus 600 further comprises an input fiber 620 to carry optical signal from the optical source. In yet another embodiment of the present invention, optical paths 602 and 610 are optical waveguides. In yet another embodiment of the present invention the apparatus further comprises a means for making comparisons of different slope measurements of the intensity-time graph. In an embodiment computer implemented means are provided for comparisons of different slope measurements of the intensity-time graph. In still another embodiment of the present invention the apparatus further comprising a refreshing means for refreshing the fluid being sampled at a predetermined sampling frequency. In an embodiment the measurements are taken on a continuous basis. However, the frequency of the data sampling may be lower in order to avoid overfilling the memory space. In an embodiment the data is saved every few minutes to every hour. The data is averaged over some period of time and the averaging period depends upon the type of the application. Those skilled in the art, however, will recognize and appreciate that the specifics of this illustrative example are not specifics of the present invention itself and that the teachings set forth herein are applicable in a variety of alternative settings. For example, since the teachings described do not depend on the number of input fibers, detectors, splitters, and optical source any number of these they can be used for achieving the objective of the present invention.

Various embodiments of the present invention provide systems and methods for optically monitoring variations in the size of the particles present in a fluid in real time. The present invention also facilities detection of onset of particle agglomeration thereby allows for timely intervention to avoid or minimize potentially high-risk circumstances of wear and damage of an engine. The embodiments of the present invention provide systems, methods and apparatus for optically monitoring variations in the size of the soot particles present in engine oil in real time. The present invention also facilities detection of onset of soot particle agglomeration and can be used with high soot generation diesel engines. This can be achieved by making successive time-spaced measurements.

The condition is monitored with reference to amount, size and state of particles present in the fluid. The user can monitor the change in the condition of the fluid with time.

In the foregoing specification, specific embodiments of the invention have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of the invention. The benefits, advantages, solutions to problems, and any element (s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method of detecting an onset of a variation in particle size in a fluid, the method comprising:

passing an optical signal from an optical source through the fluid, the optical signal comprising a signal of a predetermined wavelength;

measuring intensity attenuation of the optical signal with an optical detector at the predetermined wavelength with respect to time, wherein the intensity attenuation is observed substantially along an axis of a main optical path of the optical signal at a predetermined sampling frequency;

determining a rate of change of the intensity attenuation; and detecting the onset of the particle size variation by detecting whether the determined rate of change of the intensity attenuation has passed a threshold rate of change.

2. The method of claim 1, wherein the detecting step comprises detecting whether the rate of change is steeper than a threshold rate of change.

3. The method of claim 1, wherein the determined rate of change is indicative of increasing particle size over time.

4. The method of claim 3, wherein the detecting step comprises detecting whether the rate of change has sufficiently increased such that the onset of substantial variation in particle size is indicative of a substantial increase in particle size.

5. The method of claim 3, wherein the determining step comprises determining first and second slopes of a graph of the intensity attenuation over time at first and second predetermined times, respectively, and wherein the detecting step comprises detecting an occurrence when the second slope becomes substantially more than the first slope, and wherein the detecting step further comprises flagging an instance of the occurrence.

6. The method of claim 1, wherein the determining step comprises determining first and second rates of change of the intensity attenuation over time, and wherein the detecting step comprises comparing the first and second rates of change.

7. The method of claim 1, wherein the measuring step and determining step are implemented on a real time basis.

8. The method of claim 1, wherein the passing step comprises passing a further optical signal through the fluid, the further optical signal having a different wavelength than the first-named optical signal.

9. The method of claim 1, wherein the predetermined wavelength is selected so as to keep the ratio of the particle size to the predetermined wavelength in a predetermined range.

10. The method of claim 9, wherein the predetermined range is about 0.3 to 8.

11. The method of claim 1, wherein the predetermined wavelength of the optical signal is selected from a range of about 400 nm to 1700 nm.

12. The method of claim 1, wherein the predetermined wavelength lies in the ultraviolet region or visible region.

13. The method of claim 1, further comprising selecting the predetermined wavelength based on the particle size, an optical characteristic of the particle size in the fluid, or the refractive index of the fluid.

14. The method of claim 1, wherein the particle size corresponds with individual particles and/or particle aggregates present in the fluid.

15. The method of claim 1, wherein the particle size corresponds with soot particles present in the fluid, the soot particles comprising carbon particles and/or aggregates of carbon particles.

16. The method of 1, wherein the fluid is an engine oil.

17. The method of claim 16, wherein the intensity attenuation is measured with reference to a number of hours of operation of an engine utilizing the engine oil.

18. The method of claim 16, wherein the intensity attenuation is measured with reference to a number of revolutions of an engine utilizing the engine oil.

19. The method of claim 16, wherein the intensity attenuation is measured with reference to a number of miles traveled by a vehicle comprising an engine utilizing the engine oil.

20. The method of claim 16, wherein the intensity attenuation is measured with reference to an amount of fuel burned by an engine utilizing the engine oil.

21. The method of claim 16, wherein the intensity attenuation is measured with reference to the age of the engine oil.

22. The method of claim 1, further comprising reducing noise levels in the measured intensity attenuation via averaging before the determining step.

23. The method of claim 1, further comprising:
splitting the optical signal to monitor the optical signal before the optical signal passes through the fluid, and
adjusting the measured intensity attenuation for drift in the optical signal.

24. A method of detecting an onset of a variation in particle size in a fluid, the method comprising:
splitting an optical signal of a predetermined wavelength from an optical source onto first and second optical paths, wherein the first optical path does not pass through the fluid and the second optical path passes through the fluid;
monitoring the first optical path for optical source drift;
measuring intensity attenuation with an optical detector at the predetermined wavelength by the fluid with respect to time, wherein the intensity attenuation is observed substantially along an axis of the second optical path;
adjusting the measured intensity attenuation to reflect the optical source drift;
determining a rate of change of intensity attenuation from the adjusted sampling data; and
detecting the onset of the variation in particle size by detecting whether the rate of change of the intensity attenuation has passed a threshold rate of change.

25. The method of claim 24, wherein the detecting step comprises detecting whether the rate of change is steeper than a threshold rate of change.

26. The method of claim 24, wherein the determined rate of change is indicative of increasing particle size over time, and wherein the detecting step comprises detecting whether the rate of change has sufficiently increased such that the onset of substantial variation in particle size is indicative of a substantial increase in particle size.

27. The method of claim 24, wherein the determining step comprises determining first and second rates of change of the intensity attenuation over time, and wherein the detecting step comprises comparing the first and second rates of change.

28. The method of claim 24, wherein the distinct predetermined wavelength is selected so as to keep the ratio of the size of the particles to the wavelength in a predetermined range.

29. The method of claim 24, wherein the particles in the fluid are soot particles comprising carbon particles and/or aggregates of carbon particles.

30. The method of claim 24, wherein the fluid is an engine oil.

* * * * *